US00PP20730P3

(12) United States Plant Patent
Ruter

(10) Patent No.: US PP20,730 P3
(45) Date of Patent: Feb. 9, 2010

(54) INDIAN HAWTHORN PLANT NAMED 'RUTRHAPH1'

(50) Latin Name: *Rhaphiolepis umbellata*
Varietal Denomination: Hawthorn RutRhaph1

(75) Inventor: John Ruter, Tifton, GA (US)

(73) Assignee: University of Georgia Research Foundation, Athens, GA (US)

( * ) Notice: Subject to any disclaimer, the term of this patent is extended or adjusted under 35 U.S.C. 154(b) by 0 days.

(21) Appl. No.: 12/214,149

(22) Filed: Jun. 17, 2008

(65) Prior Publication Data

US 2009/0313733 P1 Dec. 17, 2009

(51) Int. Cl.
*A01H 5/00* (2006.01)

(52) U.S. Cl. ..... Plt./254
(58) Field of Classification Search ..... Plt./254
See application file for complete search history.

(56) References Cited

U.S. PATENT DOCUMENTS

PP19,073 P2 8/2008 Berry

*Primary Examiner*—Annette H Para
(74) *Attorney, Agent, or Firm*—Davis Wright Tremaine LLP

(57) ABSTRACT

A new and distinct cultivar of hawthorn, *Rhaphiolepis umbellata*, which is characterized by unique undulate leaf margins with small leaf margins; petite petals, with both length and width being small; overall plant height and width resulting in a small and wide appearance; relatively few stamens; relatively early full bloom date; and relatively slow growth.

2 Drawing Sheets

Figure 1:
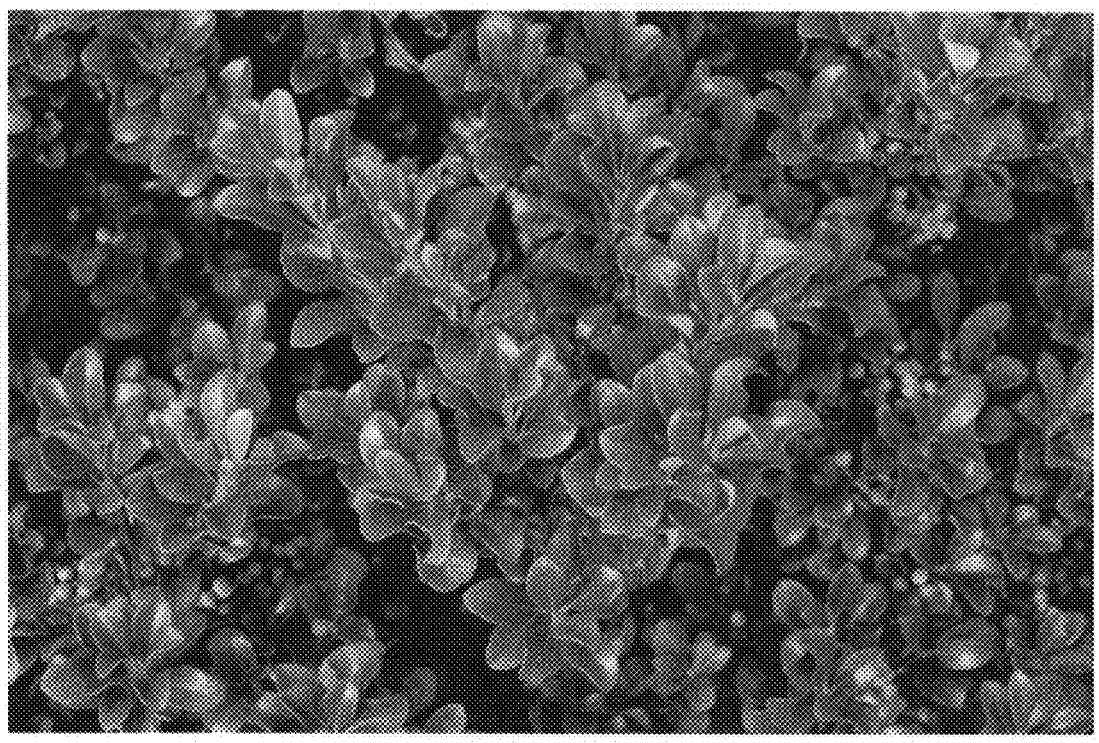

Botanical classification: *Rhaphiolepis umbellata.*
Varietal denomination: Hawthorn 'RutRhaph1'.

BACKGROUND OF THE INVENTION

The present invention relates to a new and distinct cultivar of the ornamental dwarf evergreen shrub *Rhaphiolepis umbellata*, known commonly as Indian Hawthorn, and hereafter referred to by the varietal denomination 'RutRhaph1'. In the landscape, 'RutRhaph1' can be used for foundation plantings, mass plantings, and in large containers. The plant is suited for low maintenance landscapes and performs well in coastal areas as well on dry and sandy sites.

The original plant of 'RutRhaph1' (originally designated "RA96UM-1") was grown from seed of open-pollinated *R. umbellata* 'Minor.' The seed was collected in 1996 from a field trial conducted in Tifton, Ga.

Seed were germinated at Tifton, Ga., and liners were grown. In 1997, the liners were taken to Cairo, Ga., and were grown under customary production conditions.

'RutRhaph1' was selected in 1998 for further evaluation. In autumn of 2001, 'RutRhaph1' was planted in the field at Tifton, Ga. for further evaluation. In May, 2004, semi-hardwood cuttings were collected, treated with a 1:5 dilution of Dip N' Grow (Dip N' Grow Inc., Clackamas, Oreg.) as a five-second quick dip and planted in 7.9 cm×7.9 cm plastic pots filled with pine bark and perlite (2:1, v:v) substrate.

Cuttings of 'RutRhaph1' were placed on a propagation bench in a glass greenhouse at Tifton, Ga. and received a mist frequency of 4 s every 10 min during daylight hours. Light exclusion was approximately 70%. Greenhouse control temperatures were set as 32° C. (day) and 21° C. (night). Rooting percentage was approximately 90% after 120 days, evidencing successful asexual reproduction of 'RutRhaph1'. The unique characteristics of this new cultivar are stable and reproduced true-to-type in successive generations. The new variety 'RutRhaph1' has been shown to maintain its distinguishing characteristics through successive asexual propagations by, for example, semi-hardwood cuttings placed under mist and treated with rooting hormone.

SUMMARY OF THE INVENTION

'RutRhaph1' can be compared to its parent, 'Minor.' Table 1 describes the differences between 'RutRhaph1' and its parent.

TABLE 1

Comparison of key morphological characteristics, 5 year growth, and disease ratings for *Rhaphiolepis* 'RUTRHAPH1' and *R. umbellata* 'Minor'

| | 'RUTRHAPH1' | 'Minor' |
|---|---|---|
| Leaf margin | undulate | entire |
| Leaf width (cm) | 2.0 to 3.0 | 1.5 to 2.0 |
| Petal length (cm) | 0.5 to 0.6 | 0.7 to 1.0 |
| Petal width (cm) | 0.3 to 0.4 | 0.6 to 0.7 |
| Number of stamens | 13 to 18 | 18 to 20 |
| 5 year height and width (m) | 1.4 × 2.6 | 1.7 × 2.3 |
| 5 year disease rating[z] | 1.3 | 1.5 |
| Full bloom date[y] | March 23 | April 2 |

[z]Incidence of Entomosporium leaf spot evaluated in May from 2003 thru 2007, averaged over five years according to a visual scale from 1 = no disease, 2 = 1% to 25%, 3 = 26% to 50%, 4 = 51% to 75%, and 5 = >76%.
[y]Average date of plants in full bloom, 2005 thru 2007.

'RutRhaph1' is a unique and attractive dwarf evergreen shrub with white flowers and excellent disease resistance. Terminal and sub-terminal cuttings can be rooted throughout the year as long as the plants are not flowering and semi-hardwood cuttings are taken. Plants have been successfully grown in container sizes ranging from 2.8 L to 19.6 L. Production time for a 2.8 L container is estimated to be 12 to 18 months. 'RutRhaph1' is slower growing than 'Minor'.

In the landscape, 'RutRhaph1' usually blooms around the third week of March in south Georgia. In general, 'RutRhaph1' blooms seven to 10 days before 'Minor.' Pest problems are minimal; no fireblight has been noted, and resistance to entomosporium leaf spot is excellent under field conditions. Some late season *Cercospora sp.* has been noted, but defoliation is minimal. 'RutRhaph1' has performed well for several years in USDA Hardiness zone 8a (USDA, 1990).

'RutRhaph1' plants have not been observed under all possible environmental conditions. The phenotype may vary somewhat with variations in environment such as light intensity, temperature and cultural conditions, without any variance in genotype. The following characteristics have been consistently observed over the course of several years, and, to the best knowledge of the inventor, their combination form the unique characteristics of 'RutRhaph1' as a new and distinct cultivar:

1. Unique undulate leaf margins with small leaf margins.
2. Petite petals, with both length and width being small.
3. Overall plant height and width resulting in a small and wide appearance.
4. Relatively few stamens.
5. Relatively early full bloom date.
6. Relatively slow growth.

BRIEF DESCRIPTION OF PHOTOGRAPHS

FIG. 1. A mature plant showing glossy foliage, leaf shape and density of 'RutRhaph1'.

Figure 2:
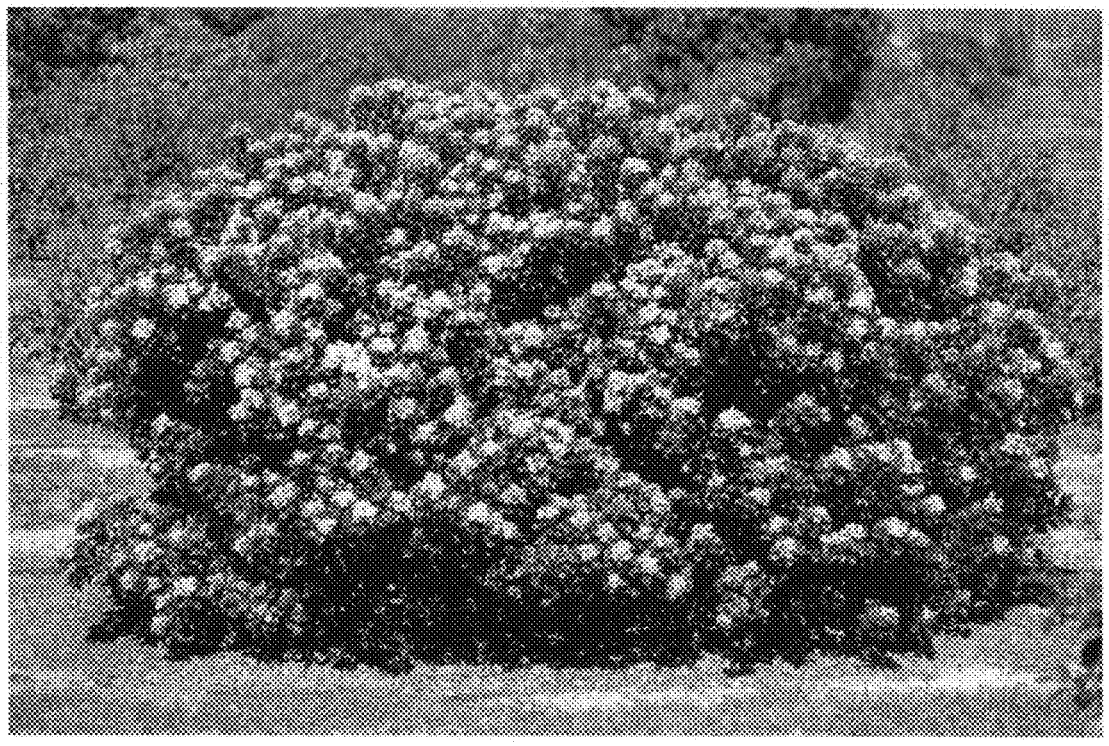

FIG. 2. A mature 'RutRhaph1' in flower, March 2007.

BOTANICAL DESCRIPTION OF THE PLANT

Unless stated otherwise, the botanical description of 'RutRhaph1' is based on five-year old plants, grown in full sun to light shade under landscape conditions in Georgia (USDA Zone 7b). Measurements are based on the average of 10 to 20 samples, and were taken throughout the main growth period, from April through September. Colors are based on The Royal Horticultural Society Chart, 2001 edition.

Plant

*Rhaphiolepis umbellata* 'RutRhaph1' is a woody, evergreen shrub which should be grown in full sun to light shade under landscape conditions in Georgia. After five years in the landscape, 'RutRhaph1' has a height of 1.4 m and spread of 2.6 m.

Stems

Stems of new growth are tardily pubescent, hairs being a greyed-white 156-D. Once the pubescence drops, color of new stems is a grey-orange 177-A, color of old stems being grey 201-A.

Leaf

Leaves are alternate, obovate in shape with undulating margins (FIG. 1), the leaf tip being obtuse and the leaf base is aequilateral. The leaves on mature shoots range from 3.5 to 5.0 cm in length, 2.0 to 3.0 cm in width, are thick and glossy and the leaf margins are slightly crenate to entire. The abaxial venation pattern of the leaves is reticulate. Adaxial leaf color (Royal Horticultural Society, 2001) is yellow-green 144-A on new growth and green 139-A on mature growth, while abaxial leaf color is yellow-green 144-C on new growth and green 138-B on mature growth. Adaxial venation color on mature plants is green 143-C, abaxial color is yellow-green 144-D. Petiole length ranges from 0.6 cm to 1.0 cm, petiole width is 0.3 cm and petiole color is green 143-C.

Inflorescence

Inflorescence a panicle, flowers on a given branch 9 to 13, not all at anthesis at the same time, flowers bisexual. Flower diameter approximately 2.0 cm. Petal number is five, petal shape obelliptic, margins entire, petal tip rounded to acute. Length of petals is 0.5 cm to 0.6 cm with a width of 0.3 cm to 0.4 cm. Petals (top and bottom) are white 155-D. Number of sepals is five, lanceolate in shape, margins pubescent with acute sepal tips. Sepal color initially yellow-green N144-A, turning red-purple 59-B as the flower matures. Sepals are 0.5 cm in length and 0.2 cm in width. Flower bud length is 0.5 to 0.6 cm with a diameter of 0.3 cm. Flower bud shape is oblong to oblanceolate. Stamen number ranges from 13 to 18, anther size being 0.13 cm, anther color is yellow 11-C. Color of pollen is yellow 9-C. Stigmatic color is yellow-green 145-C. Length of styles is 0.37 cm, color being yellow-green 145-C.

Fruit

Fruit a greyed-purple (N186-A) pome, two locules per ovary, one to two seed per fruit. Fruit diameter is 0.75 to 0.95 cm, fruit length ~0.7 cm. Fruit ripening in October in Tifton, Ga. Holotype: field grown plant, Ornamental Horticulture Research Area, University of Georgia, Tifton, Ga., *Hand and Ruter* (VSC). Isotype: NA.

Seed

Seed color is greyed-orange 176-A, length and width 0.6 cm.

It is claimed:

1. We claim a new and distinct variety of Indian Hawthorn plant named 'RutRhaph1' substantially as herein described and illustrated.

* * * * *